United States Patent
Collins et al.

(10) Patent No.: US 6,853,704 B2
(45) Date of Patent: Feb. 8, 2005

(54) SYSTEM PROVIDING MULTIPLE FOCUSED RADIATION BEAMS

(75) Inventors: William F. Collins, Clayton, CA (US); Christopher Jude Amies, Walnut Creek, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 85 days.

(21) Appl. No.: 10/252,911

(22) Filed: Sep. 23, 2002

(65) Prior Publication Data

US 2004/0057552 A1 Mar. 25, 2004

(51) Int. Cl.[7] ............................................. A61N 5/10
(52) U.S. Cl. .................................... 378/65; 378/84
(58) Field of Search ............................. 378/65, 84, 85

(56) References Cited

U.S. PATENT DOCUMENTS

| | | | |
|---|---|---|---|
| 1,865,441 A | 7/1932 | Mutscheller | |
| 2,557,662 A | 6/1951 | Kirkpatrick | |
| 5,604,782 A | 2/1997 | Cash, Jr. | |
| 6,125,295 A | 9/2000 | Cash, Jr. et al. | |
| 6,195,410 B1 | 2/2001 | Cash, Jr. | |
| 6,359,963 B1 * | 3/2002 | Cash ........................... | 378/65 |
| 6,366,801 B1 | 4/2002 | Cash, Jr. et al. | |
| 6,438,203 B1 * | 8/2002 | Shipeng et al. ............... | 378/65 |
| 6,512,813 B1 * | 1/2003 | Krispel et al. ................ | 378/65 |
| 2001/0043667 A1 | 11/2001 | Antonell et al. | |

OTHER PUBLICATIONS

"Highly Oriented Pyrolytic Graphite", download from http://www.win.ne.ip/~techno/e HOPG.html on Jul. 29, 2002. 1 pg.
"Overview of Cancer and Radiation Therapy", downloaded from http://www.vetradtherapy.com/overview.html on Jul. 24, 2002. 6 pgs.

* cited by examiner

Primary Examiner—Craig E. Church (57) ABSTRACT

A system includes a plurality of treatment heads, each of the plurality of treatment heads including a radiation source and a radiation-focusing lens. The system also includes a plurality of voltage sources, each of the plurality of voltage sources associated with a respective one of the plurality of treatment heads, and a control device to control an intensity of radiation emitted from each radiation-focusing lens of the plurality of treatment heads in accordance with a treatment plan.

20 Claims, 6 Drawing Sheets

SYSTEM PROVIDING MULTIPLE FOCUSED RADIATION BEAMS

BACKGROUND

1. Field

The present invention relates generally to medical treatment using focused radiation, and more particularly to systems for delivering such treatment.

2. Description

Conventional radiation treatment typically involves directing a radiation beam at a tumor located within a patient. The radiation beam is intended to deliver a predetermined dose of treatment radiation to the tumor according to an established treatment plan. The goal of such treatment is to kill tumor cells through ionizations caused by the radiation.

In conventional radiation treatment systems, a linear accelerator generates a divergent beam of photons having energies in excess of 1 MeV. A patient is positioned such that the beam is directed toward a treatment area of the patient. The beam may be shaped by beam-shaping devices before reaching the treatment area in an attempt to ensure that beam closely matches the shape of the treatment area and does not harm healthy tissue. Accordingly, an oncologist plans conventional treatment with megavoltage radiation by considering the divergence of the beam, the distance over which the beam travels to the treatment area, and known data representing organs and other structures internal to the patient.

Treatment systems using kilovoltage radiation may possess several advantages over the above-described treatment systems using megavoltage radiation. For example, the beam-generating hardware used in kilovoltage treatment systems may be much cheaper, simpler and more reliable than that used in megavoltage treatment systems. Environmental safety is of less concern with kilovoltage treatment systems, which typically require 3 mm of lead shielding as opposed to the 2 m of concrete shielding required for megavoltage treatment systems. Moreover, kilovoltage radiation may be more precisely targeted because it engenders less penumbra and less target overshoot than megavoltage radiation.

Despite the foregoing, megavoltage radiation has been preferred over kilovoltage radiation for use in radiation treatment. One reason for this preference is the difference in tissue-damaging mechanisms associated with each type of radiation. Megavoltage radiation damages tissue mostly through high-energy electrons created by Compton scattering of high-energy photons. These electrons penetrate inward from the site of radiation/tissue interaction, causing little damage to tissue at the surface of the interaction (e.g., skin) relative to the damage caused at a deeper target area.

In contrast, most tissue damage caused by kilovoltage radiation results from photoelectric absorption. For a given energy per unit area, damage resulting from photoelectric absorption is greatest at the surface of a radiation/tissue interaction and decreases with depth into the tissue. Consequently, a kilovotage radiation beam of uniform or decreasing energy per unit area (i.e., a divergent beam) may cause greater tissue damage at a patient's skin than at a treatment area within the patient's body.

Many techniques exist for addressing this drawback of kilovoltage radiation treatment. A kilovoltage radiation treatment system such as those described in U.S. Pat. No. 6,366,801 to Cash et al uses a radiation source which produces a divergent beam of traditional medical x-rays having energies in the 50 to 150 keV range and focuses the beam on a target area using a lens designed for this purpose. By focusing the radiation, the energy per unit area increases with proximity to the target area. As a result, tissue damage at a portion of the target area may be greater than tissue damage at a same-sized portion of the radiation/skin interaction site. Attempts to increase this relative difference in tissue damage include developing lenses that focus the radiation at greater and greater angles of convergence and/or injecting radiation-absorbing contrast agents at the target area.

Also proposed are methods in which a patient is positioned, a target area is irradiated by a radiation beam, the patient is repositioned such that a subsequent radiation beam would intercept an area of the patient's skin that was not irradiated by the previous radiation beam, and the target is irradiated again. The patient may be repositioned and the target irradiated several times. Still other methods include moving the radiation beam so as to scan the target area. None of these attempts have proved to be satisfactorily efficient and/or effective.

SUMMARY

To address the foregoing, some embodiments of the present invention provide a system, method, apparatus, and means to transmit radiation from a plurality of radiation sources to respective ones of a plurality of radiation-focusing lenses, and to focus the transmitted radiation on a target area with the plurality of radiation-focusing lenses.

In some embodiments, the present invention provides a plurality of radiation sources, and a plurality of radiation-focusing lenses, each of the plurality of radiation-focusing lenses associated with a respective one of the plurality of radiation sources.

The present invention relates to, in some embodiments, a system including a plurality of treatment heads, with each of the plurality of treatment heads including a radiation source and a radiation-focusing lens. Also included are a plurality of voltage sources, each of the plurality of voltage sources associated with a respective one of the plurality of treatment heads, and a control device to control an intensity of radiation emitted by each radiation-focusing lens of the plurality of treatment heads in accordance with a treatment plan.

The present invention is not limited to the disclosed embodiments, however, as those of ordinary skill in the art can readily adapt the teachings of the present invention to create other embodiments and applications.

BRIEF DESCRIPTION OF THE DRAWINGS

The exact nature of this invention, as well as its objects and advantages, will become readily apparent from consideration of the following specification as illustrated in the accompanying drawings, in which like reference numerals designate like parts, and wherein.

DETAILED DESCRIPTION

The following description is provided to enable any person of ordinary skill in the art to make and use the invention and sets forth the best modes contemplated by the inventors for carrying out the invention. Various modifications, however, will remain readily apparent to those in the art.

Figure 1:
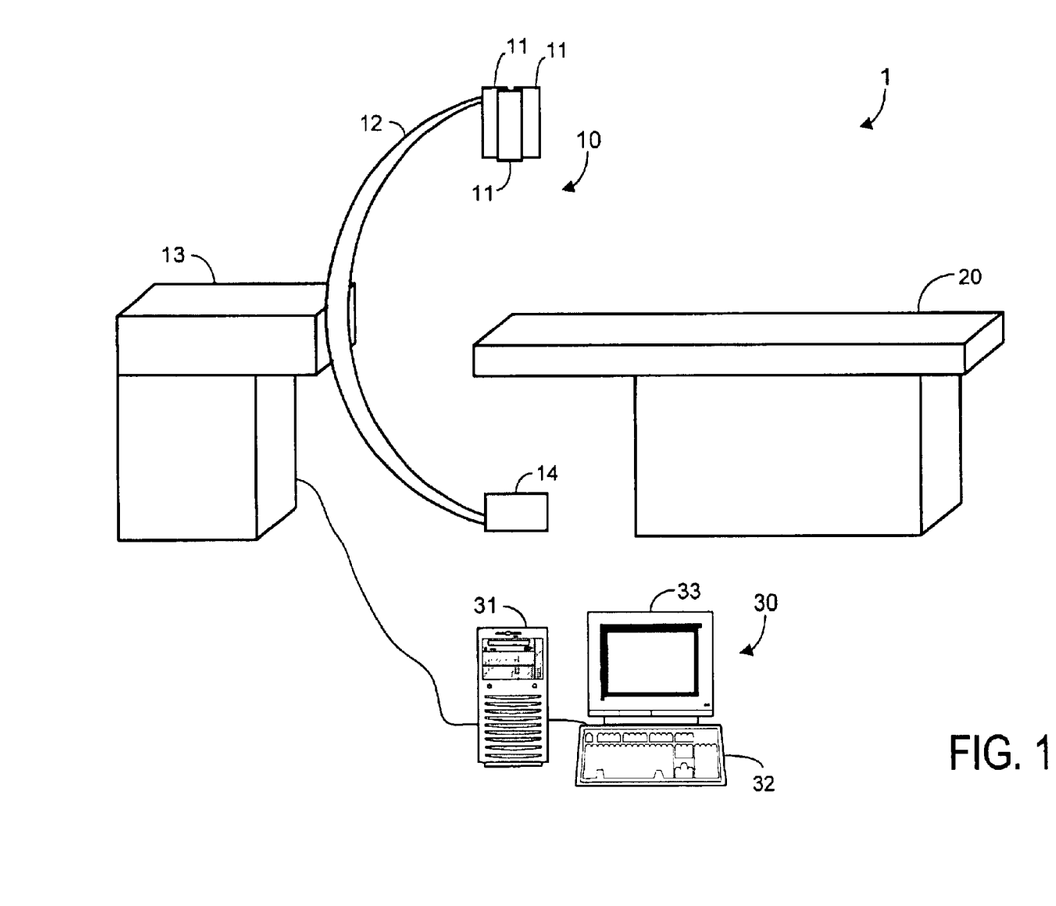
FIG. 1 is a diagram illustrating a radiation treatment room according to some embodiments of the present invention.

FIG. 1 illustrates radiation treatment room 1 pursuant to some embodiments of the present invention. Radiation treatment room 1 includes kilovoltage radiation treatment unit 10, treatment table 20 and operator station 30. The elements of radiation treatment room 1 are used to deliver kilovoltage radiation to a patient according to a treatment plan. In this regard, kilovoltage radiation refers herein to any radiation having energies ranging from 50 to 150 keV. However, it should be noted that some embodiments of the present invention may be used in conjunction with any focused radiation beam.

Treatment unit 10 is used to deliver treatment radiation to a treatment area and includes treatment heads 11, c-arm 12, base 13 and imaging system 14. Treatment unit 10 includes seven treatment heads 11 but embodiments of the invention are not limited to this number. Each treatment head 11 includes a radiation source such as an x-ray tube for emitting kilovoltage radiation used during calibration and/or treatment. The radiation may comprise electron, photon or any other type of radiation. Each treatment head 11 also includes a cylinder in which are disposed the radiation source, a radiation-focusing lens for focusing radiation emitted by an associated radiation source, and an aperture for changing a shape and/or intensity of the focused radiation. Treatment head 11 according to some embodiments of the invention will be described in more detail below with respect to FIG. 2.

C-arm 12 is slidably mounted on base 13 and can therefore be moved in order to change the position of treatment heads 11 with respect to table 20 and, more particularly, with respect to a patient lying on table 20. In some embodiments, base 13 also includes one or more voltages sources such as high-voltage generators for supplying power used by treatment heads 11 to generate kilovoltage radiation. One or more treatment heads 11 may be associated with one or more voltage sources. Many c-arm/base configurations may be used in conjunction with some embodiments of the present invention, including configurations in which base 13 is rotatably mounted to a ceiling of room 1, configurations in which one c-arm is slidably mounted on another c-arm, and configurations incorporating multiple independent c-arms.

Examples of c-arm kilovoltage radiation units include Siemens SIREMOBIL™, MULTISTAR™, BICOR™ and POLYSTAR™ units as well as other units designed to perform tomography and/or angiography. These units are often less bulky and less costly than megavoltage radiation systems. Of course, any system for delivering a focused radiation beam may be used in conjunction with some embodiments of the present invention.

Imaging system 14 produces an image based on the radiation emitted by treatment heads 11. The image reflects the attenuative properties of objects located between treatment heads 11 and imaging system 14 while the radiation is emitted. Imaging system 14 may comprise an image intensifier and a camera. An image intensifier is a vacuum tube that converts X-rays to visible light, which is then detected by the camera to produce an image. Imaging system 14 may also comprise a flat-panel imaging system that uses a scintillator and silicon sensor elements or direct x-ray conversion mechanisms to produce an image based on received radiation.

A patient is placed on treatment table 20 during treatment in order to position a target area between treatment heads 11 and imaging system 14. Accordingly, table 20 may comprise mechanical systems for moving itself with respect to unit 10.

Operator station 30 includes processor 31 in communication with an input device such as keyboard 32 and an output device such as operator display 33. Operator station 30 is typically operated by an operator who administers actual delivery of radiation treatment as prescribed by an oncologist. Operator station 30 may be located apart from treatment unit 10, such as in a different room, in order to protect the operator from radiation. It should be noted, however, that kilovoltage radiation treatment does not require protective measures to the extent of those taken during megavoltage radiation therapy, resulting in less costly therapy.

Processor 31 may store processor-executable process steps according to some embodiments of the present invention. In some aspects, the process steps are executed by operator station 30, treatment unit 10, imaging system 14, and/or another device to transmit radiation from a plurality of radiation sources to respective ones of a plurality of radiation-focusing lenses, and to focus the transmitted radiation on a target area with the plurality of radiation-focusing lenses. The process steps may also be executed to adjust a voltage supplied to at least one of the plurality of radiation sources, to engage an aperture associated with at least one of the plurality of radiation sources, to control an intensity of radiation emitted by each of the plurality of radiation-focusing lenses in accordance with a treatment plan, and/or to move at least one of the plurality of radiation sources with respect to at least one other of the plurality of radiation sources in accordance with a treatment plan.

The above-described steps may also be embodied, in whole or in part, by hardware and/or firmware of processor 31, treatment unit 10, treatment heads 11, imaging system 14, and another device. Of course, each of the devices shown in FIG. 1 may include less or more elements than those shown. In addition, embodiments of the invention are not limited to the devices shown.

Figure 2:
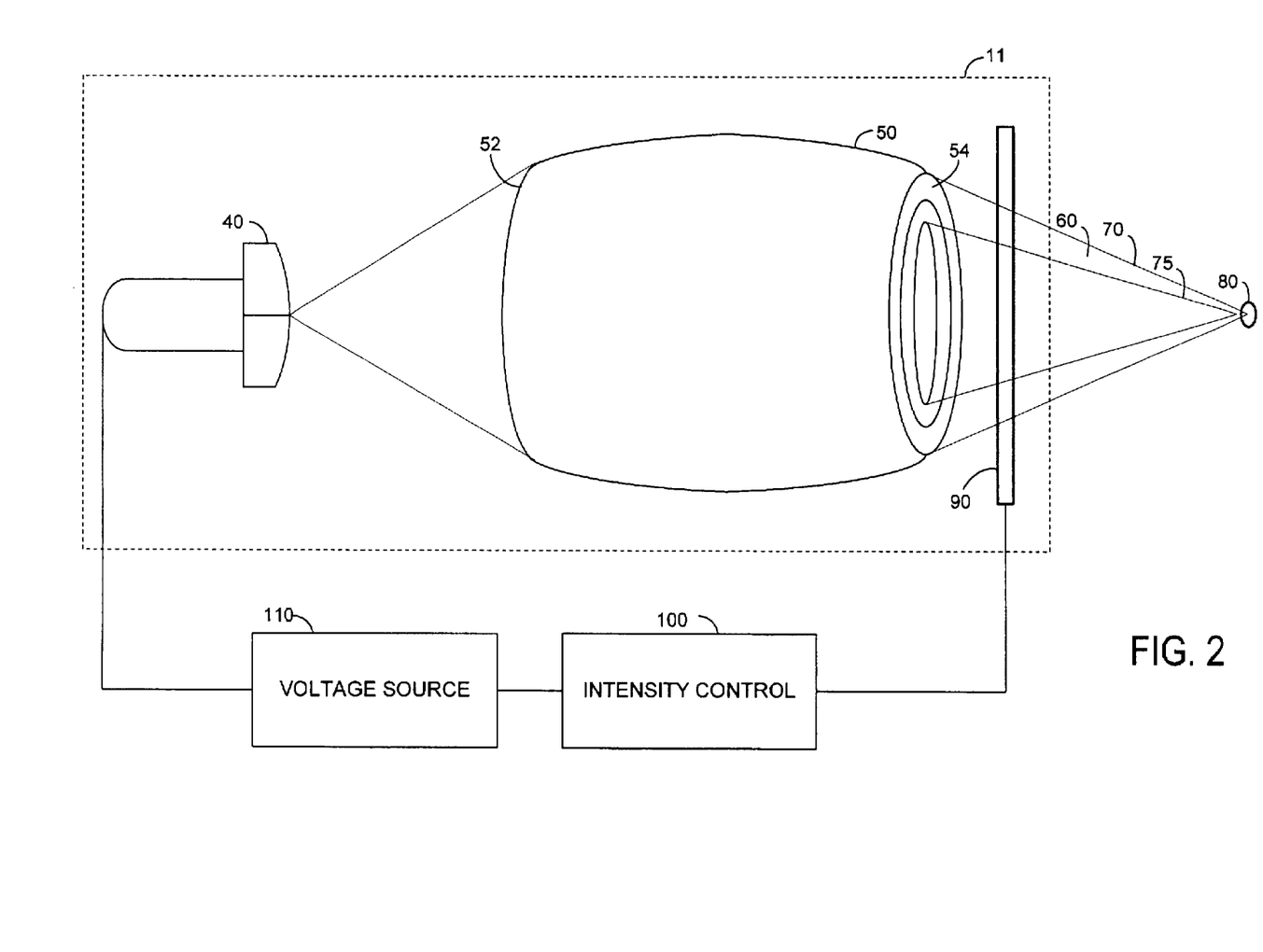
FIG. 2 is a diagram illustrating elements of and related to a treatment head according to some embodiments of the present invention.

FIG. 2 is a representative view of elements of treatment head 11 according to some embodiments of the present invention. It should be noted that the neither the elements nor their physical relationships to one another are necessarily drawn to scale. As shown, treatment head 11 includes x-ray tube 40 for emitting radiation toward lens 50. In some embodiments, x-ray tube 40 comprises a Diabolo™ x-ray tube. The radiation enters entry surface 52 of lens 50 and some or all of the radiation exits exit surface 54. In this regard, the radiation energy exiting exit surface 54 may comprise 10% or less of the total radiation energy striking entry surface 52.

Lens 50 may comprise any radiation-focusing lens, including those having a shape different from that illustrated. In this regard, lens 50 of FIG. 2 comprises strips of reflective material arranged in the form of several barrels nested around a central axis. Each "barrel" is separated from adjacent "barrels" by Plexiglas or another optically neutral substrate. Lens 50 may also comprise any other radiation-focusing lenses such as those described in U.S. Pat. No. 6,359,963 to Cash, in U.S. Pat. No. 5,604,782 to Cash, Jr., in U.S. Patent Application Publication No. 2001/0043667 of Antonell et al., and/or elsewhere in currently or hereafter-known art.

Highly Oriented Pyrolitic Graphite (HOPG) may be used as the reflective material of lens 50. HOPG consists of planes of carbon atoms that are highly oriented toward one another. In the ideal variant, these planes are parallel to one another.

By virtue of the composition, shape and construction of lens 50 and of properties of the radiation emitted by x-ray tube 40, radiation exiting from exit surface 54 substantially follows radiation path 60. Geometrically, path 60 comprises a hollow conical volume between outer cone surface 70 and inner cone surface 75. Of course, different radiation-focusing lenses used in conjunction with embodiments of the invention may direct radiation along differently-shaped paths.

Lens 50 operates to substantially focus all or a portion of the directed radiation on focal area 80. Focal area 80 may comprise a point in space or a larger area. In some embodiments of lens 50, focal area 80 is approximately 1 cm in diameter. According to the FIG. 2 embodiment, focal area 80 is spaced from an exit surface of lens 50 by a distance determined by the composition, shape and construction of lens 50 as well as by characteristics of the radiation emitted by x-ray tube 40.

It should be noted that path 60 might not terminate at focal area 80. Rather, path 60 may continue thereafter, becoming further attenuated and unfocused as its distance from focal area 80 increases. In some embodiments, the divergence of path 60 from focal area 80 roughly mirrors its convergence thereto.

Treatment head 11 also includes aperture 90 for blocking all or a portion of radiation exiting from exit surface 54. Aperture 90 may block the radiation using a material such as lead which completely attenuates incident radiation and/or another material which partially attenuates incident radiation. Treatment head 11 may include elements for engaging aperture 90 between lens 50 and focal area 80 and for disengaging aperture 90 therefrom. Aperture 90 may comprise elements that are controllable to change its blocking characteristics, including movable patterns composed of alternative blocking materials. Aperture 90 may comprise beam-shaping devices such as one or more jaws, collimators, and reticles. Moreover, aperture 90 may be located between x-ray tube 40 and lens 50.

Aperture 90 may be engaged by intensity control 100 to control an intensity of radiation emitted from lens 50. In this regard, intensity control 100 may operate to move aperture 90 between lens 50 and focal area 80 and/or to issue to configure elements within aperture 90 in accordance with a radiation treatment plan. Such operations may be performed in conjunction with associated elements of treatment head 11, and may simply comprise issuing instructions to conduct the operations. Intensity control 100 may comprise one or more of software, hardware, and firmware elements located in one or more of processor 31, treatment head 11, base 13, a stand-alone device, or another device.

Intensity control 100 may also instruct voltage source 110 to control an intensity of radiation emitted by x-ray tube 40 in accordance with a radiation treatment plan. Voltage source 110 may be dedicated to x-ray tube 40 of FIG. 2 or may provide voltage to one or more other x-ray tubes of treatment unit 10. Of course, voltage source 110 and aperture 90 might not be controlled by a same control unit. Voltage source 110 may be located in base 13 or elsewhere.

Figure 3:
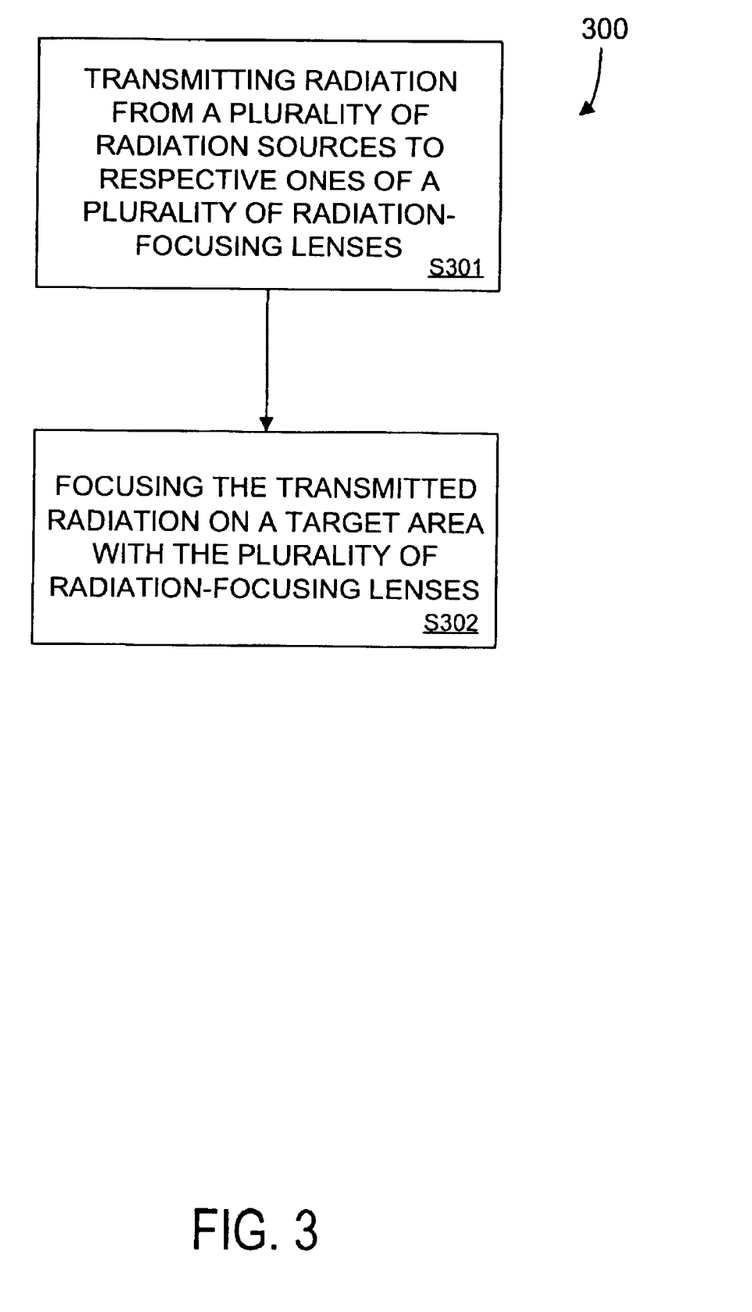
FIG. 3 comprises a flow diagram illustrating process steps according to some embodiments of the present invention.

FIG. 3 comprises a flow diagram of process steps 300 according to some embodiments of the invention. Process steps 300 may be embodied by hardware, firmware, and/or software of processor 31, treatment unit 10, and/or another device.

Process steps 300 begin at step S301, in which radiation is transmitted from a plurality of radiation sources to respective ones of a plurality of radiation-focusing lenses. According to one specific example of step S301, x-ray tube 40 is activated to transmit radiation to lens 50 and the five other x-ray tubes of treatment unit 10 are similarly activated to transmit radiation to radiation-focusing lenses associated therewith. In some embodiments, intensity control 100 adjusts a voltage supplied to x-ray tube 40 and/or one or more x-ray tubes according to a treatment plan by controlling voltage source 110 and/or one or more other voltage sources associated with the one or more x-ray tubes. As a result, intensity control 100 controls an intensity of radiation emitted by x-ray tube 40 and/or one or more x-ray tubes according to the treatment plan.

Figure 4A:
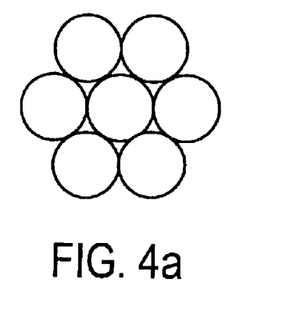
FIGS. 4a through 4f each comprise a view of a multiple treatment head configuration according to some embodiments of the present invention.
Figure 4B:
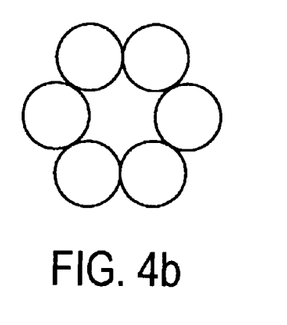
Figure 4C:
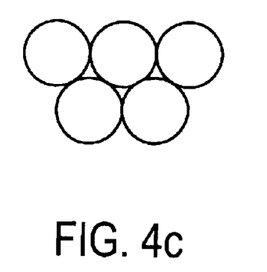
Figure 4D:
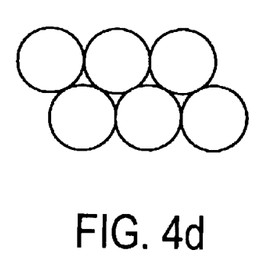
Figure 4E:
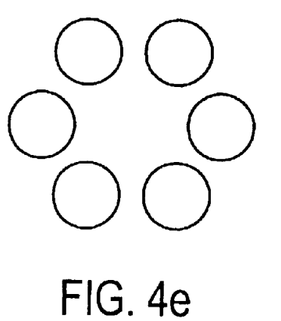
Figure 4F:
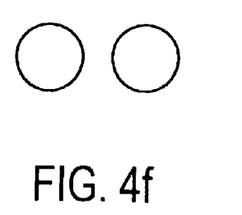

FIGS. 4a through 4f illustrate treatment head configurations according to some embodiments of the invention. Each configuration includes a plurality of radiation sources and a plurality of radiation-focusing lenses, with each of the plurality of radiation-focusing lenses associated with a respective one of the plurality of radiation sources. FIG. 4a illustrates a seven-treatment head configuration as described in regards to FIG. 1. The remaining configurations of FIGS. 4b through 4f are merely illustrative and are not intended to limit the configurations usable in conjunction with some embodiments of the present invention. As described above, some embodiments do not utilize any treatment heads.

In step S302, lens 50 and at least one other radiation-focusing lens focus the transmitted radiation on a target area. Each lens used in step S302 may focus radiation on a focal area located within the target area. Each focal area might not overlap any other focal area, or one or more of the focal areas might overlap one or more other of the focal areas.

As described above, aperture 90 may be engaged so as to block all or a portion of radiation exiting from exit surface 54. Apertures associated with one or more other radiation-focusing lenses used in step S302 may also be engaged to block all or a portion of radiation exiting from associated lenses. Such engagement may also be controlled by intensity control 110 in accordance with a treatment plan.

Figure 5A:
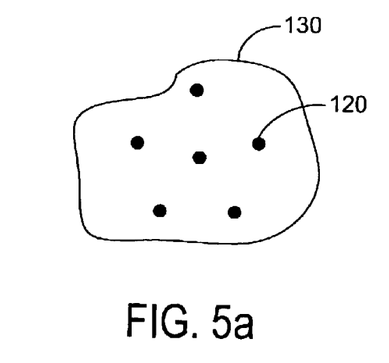
FIGS. 5a through 5d each comprise an illustration of radiation delivery to a target according to some embodiments of the present invention.

FIGS. 5a through 5d show focal areas 120 of radiation delivered to target area 130 in accordance with four different treatment plans. The position of focal areas 120 corresponds to one example of the head configuration shown in FIG. 4a. FIG. 5a illustrates a treatment plan in which full-intensity radiation is emitted from a radiation-focusing lens of each treatment head.

Figure 5B:
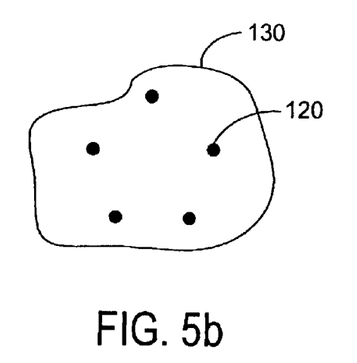

FIG. 5b illustrates a treatment plan in which full-intensity radiation is emitted from a radiation-focusing lens of each outermost treatment head but in which no radiation is emitted from a radiation-focusing lens of the innermost treatment head. As described above, the FIG. 5b treatment plan may be achieved by adjusting a voltage supplied to a radiation source of the innermost treatment head such that no radiation is emitted therefrom. The FIG. 5b plan may also be achieved by engaging a radiation-blocking aperture of the innermost treatment head.

Figure 5C:
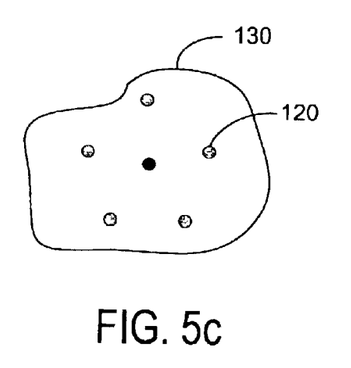

The FIG. 5c treatment plan requires full-intensity radiation emitted from a radiation-focusing lens of the innermost treatment head, and less than full-intensity radiation emitted from radiation-focusing lenses of the outermost treatment heads. Less than full-intensity may be achieved by adjusting an x-ray tube current supplied to a radiation source of zero or more of the outermost treatment heads such that no radiation is emitted therefrom and by engaging an aperture for partially attenuating radiation of remaining ones of the outermost treatment heads. Of course, an intensity of radiation emitted from a radiation-focusing lens may be controlled by adjusting an x-ray tube current supplied to a radiation source associated with the lens and by engaging an aperture associated with the lens.

Figure 5D:
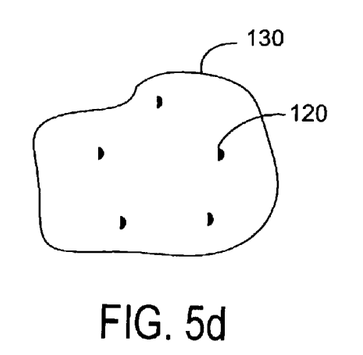

FIG. 5d illustrates a treatment plan in which an aperture associated with each treatment head is engaged so as to block one half of the radiation emitted from a radiation-focusing lens associated with each treatment head. As a result, the intensity of the emitted radiation has been decreased by one half. Of course, aperture patterns other than that shown in FIG. 5d may be used to block one half of the radiation emitted from a radiation-focusing lens.

Figure 6:
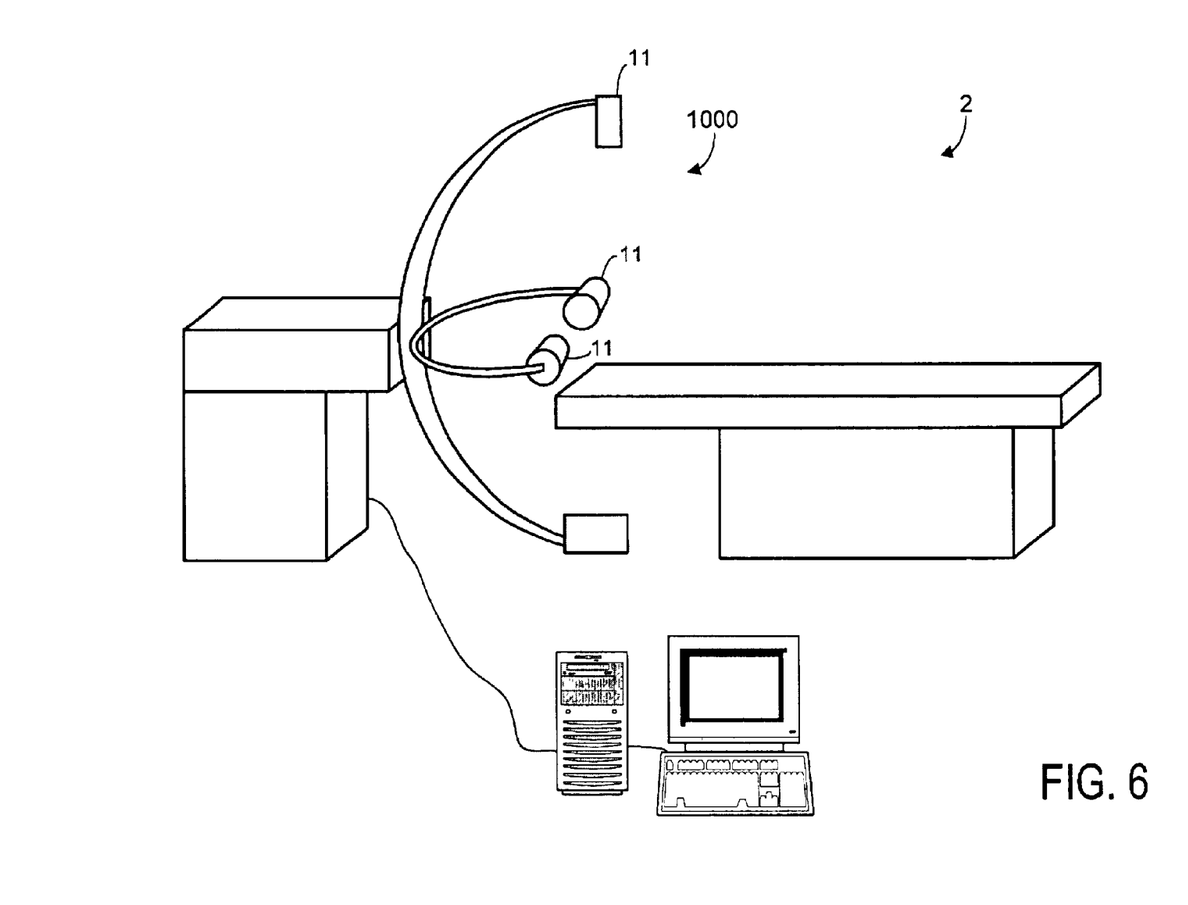
FIG. 6. is a diagram illustrating a radiation treatment room according to some embodiments of the present invention.

FIG. 6 is a diagram illustrating radiation treatment room 2 according to some embodiments of the present invention. Treatment room 2 is includes treatment unit 1000. In contrast to treatment unit 10 of treatment room 1, treatment unit 1000 includes three treatment heads 11 mounted to respective ones of three physical extensions. Treatment head configurations other than those described herein may be used in conjunction with some embodiments of the present invention. For example, some embodiments of the invention comprise at least one treatment head that may be moved with relative to at least one other treatment head.

In this regard, it should be noted that embodiments of the invention are not limited to the arrangements described above. For example, a treatment head may include more than one radiation source and/or more than one associated radiation-focusing lens. Moreover, a treatment head used in conjunction with some embodiments of the invention may be shaped differently than as described herein, and some embodiments may use two or more treatment heads having different shapes and/or configurations. In addition, a single aperture may be used to fully and/or partially block radiation emitted from two or more radiation-focusing lenses. A single intensity control unit may be used to control such an aperture. Of course, one or more dedicated intensity control units may control the intensity of radiation emitted from a treatment head.

Generally, those in the art will appreciate that various adaptations and modifications of the above-described embodiments can be configured without departing from the scope and spirit of the invention. Therefore, it is to be understood that, within the scope of the appended claims, embodiments of the invention may be practiced other than as specifically described herein.

What is claimed is:

1. An apparatus comprising:
   a plurality of X-ray radiation sources;
   a plurality of X-ray radiation-focusing lenses, each of the plurality of X-ray radiation-focusing lenses associated with a respective one of the plurality of X-ray radiation sources; and
   control elements to control a characteristic of X-ray radiation delivered to a target area from one of the plurality of X-ray radiation sources to differ from a characteristic of X-ray radiation delivered to the target area from at least one other of the plurality of X-ray radiation sources.

2. An apparatus according to claim 1, further comprising:
   a plurality of voltage sources, each of the plurality of voltage sources associated with a respective one of the plurality of X-ray radiation sources.

3. An apparatus according to claim 1, the control elements comprising:
   a control device associated with the one of the plurality of X-ray radiation sources.

4. An apparatus according to claim 3, wherein the control device is operable to adjust a current supplied to the one of the plurality of X-ray radiation sources.

5. An apparatus according to claim 3, the control elements further comprising:
   an aperture associated with the one of the plurality of X-ray radiation sources to control a shape of the X-ray radiation delivered to the target area from the one of the plurality of X-ray radiation sources,
   wherein the control device is operable to engage the aperture.

6. An apparatus according to claim 1, the control elements further comprising an aperture to control a shape of the X-ray radiation delivered to the target area from the one of the plurality of X-ray radiation sources.

7. An apparatus according to claim 1, the control elements comprising a control device to control an intensity of X-ray radiation emitted from each of the plurality of X-ray radiation-focusing lenses in accordance with a treatment plan.

8. An apparatus according to claim 1, wherein each of the plurality of X-ray radiation sources is fixed with respect to each other of the plurality of X-ray radiation sources.

9. An apparatus according to claim 1, wherein at least one of the plurality of X-ray radiation sources is movable relative to at least one other of the plurality of X-ray radiation sources.

10. A method comprising:
    transmitting X-ray radiation from a plurality of X-ray radiation sources to respective ones of a plurality of X-ray radiation-focusing lenses;
    focusing the transmitted X-ray radiation on a target area with the plurality of X-ray radiation-focusing lenses; and
    controlling a characteristic of X-ray radiation transmitted from one of the plurality of X-ray radiation sources to differ from a characteristic of X-ray radiation transmitted from at least one other of the plurality of X-ray radiation sources.

11. A method according to claim 10, wherein each of the plurality of X-ray radiation-focusing lenses focuses X-ray radiation on respective ones of a plurality of focal areas.

12. A method according to claim 11, wherein none of the plurality of focal areas intersects any other of the plurality of focal areas.

13. A method according to claim 10, wherein the controlling step comprises adjusting a current supplied to the one of the plurality of X-ray radiation sources to differ from a current supplied to the at least one other of the plurality of X-ray radiation sources.

14. A method according to claim 10, wherein the controlling step comprises engaging an aperture to control a shape of the X-ray radiation transmitted from the one of the plurality of X-ray radiation sources to differ from a shape of the X-ray radiation transmitted from the at least one other of the plurality of X-ray radiation sources.

15. A method according to claim 10, wherein the controlling step comprises controlling an intensity of the X-ray radiation transmitted from the one of the plurality of X-ray radiation sources to differ from an intensity of the X-ray radiation transmitted from the at least one other of the plurality of X-ray radiation sources.

16. A method according to claim 10, further comprising moving at least one of the plurality of X-ray radiation sources with respect to at least one other of the plurality of X-ray radiation sources in accordance with a treatment plan.

17. A computer-readable medium storing computer-executable process steps, the process steps comprising:
- a step to transmit X-ray radiation from a plurality of X-ray radiation sources to respective ones of a plurality of X-ray radiation-focusing lenses;
- a step to focus the transmitted X-ray radiation on a target area with the plurality of X-ray radiation-focusing lenses; and
- a step to control a characteristic of X-ray radiation transmitted from one of the plurality of X-ray radiation sources to differ from a characteristic of X-ray radiation transmitted from at least one other of the plurality of X-ray radiation sources.

18. A system comprising:
- a plurality of treatment heads, each of the plurality of treatment heads comprising:
  - an X-ray radiation source; and
  - an X-ray radiation-focusing lens;
- a plurality of voltage sources, each of the plurality of voltage sources associated with a respective one of the plurality of treatment heads; and
- a control device to control an intensity of X-ray radiation emitted by one of the plurality of X-ray radiation-focusing lenses to differ from an intensity of X-ray radiation emitted by at least one other of the plurality of X-ray radiation-focusing lenses in accordance with a treatment plan.

19. A system according to claim 18, wherein the control device controls the intensity of the X-ray radiation emitted from the one X-ray radiation-focusing lens by controlling a voltage source associated with the one X-ray radiation-focusing lens.

20. A system according to claim 18, wherein the control device controls the intensity of the X-ray radiation emitted from the one X-ray radiation-focusing lens by engaging an aperture associated with the one X-ray radiation-focusing lens.

* * * * *